(12) United States Patent
Rentzepis et al.

(10) Patent No.: US 6,693,201 B1
(45) Date of Patent: Feb. 17, 2004

(54) FLUORESCENT PHOTOCHROMIC FULGIDES, PARTICULARLY FOR OPTICAL MEMORIES

(75) Inventors: Peter M. Rentzepis; Alexander Dvornikov, both of Irvine, CA (US)

(73) Assignee: The Regents Of the University of California, Oakland, CA (US)

( * ) Notice: Subject to any disclaimer, the term of this patent is extended or adjusted under 35 U.S.C. 154(b) by 0 days.

(21) Appl. No.: 09/391,280

(22) Filed: Sep. 7, 1999

Related U.S. Application Data (60) Provisional application No. 60/099,513, filed on Sep. 8, 1998.

(51) Int. Cl.⁷ .............................................. C07D 405/06
(52) U.S. Cl. ....................................... 548/468; 549/472
(58) Field of Search ................................ 548/490, 517, 548/468; 549/472, 476, 477

(56) References Cited

FOREIGN PATENT DOCUMENTS

| JP | 02160779 | * 12/1988 |
| JP | 63166877 | * 12/1988 |

OTHER PUBLICATIONS

Siebold et al., Mol. Cryst. Liq. Cryst. Sci. Technol., Sect. A, p. 283—Abstract only, 1996.*
Santiago et al., J. Amer. Chem. Soc., 90(14), pp. 3654–3658—Abstract only, 1996.*
Hackh's Chemical Dictionary, Julius Grant, Ed.; McGraw–Hill Book Company, New York (1969) pp. 273–274, 516.*
Translation, JP 02160779 to Yamaha Co., Ltd., Suzuki et al. (Jun. 20, 1990).*
Yokoyama et al., "Chiral Photochromic Compounds and Control of Functions," Enantiomer, vol. 3(2), pp. 123–132, 1998.*
Santiago et al., "Photochromic Fulgides. Spectroscopy and Mechanism of Reactions," J. Am. Chem. Soc., 90(14), pp. 3654–3658, 1998.*

* cited by examiner

*Primary Examiner*—Robert W. Ramsuer
*Assistant Examiner*—Kamal Saeed
(74) *Attorney, Agent, or Firm*—Fuess & Davidenas (57) ABSTRACT

Photochromic chemicals consisting essentially of colored fluorescent heterocyclic fulgides are particularly suitable for optical memories. The preferred heterocyclic photochromic fulgides consist essentially of colored 2-indolyfulgides capable of excitation by ultraviolet light to fluoresce. These heterocyclic photochromic fulgides are preferably synthesized by process of (1) condensation of 1,3-dimethyl-(5-substituted)indole-2-carboxaldehyde with diethyl IV iospropylidenesuccinate as a key intermediate; followed by (2) hydrolysis; and (3) intramolecular acid anhydride formation.

1 Claim, 6 Drawing Sheets

Fig. 1

Scheme 1a  Fig. 2a

R = OCH$_3$ (a), CH$_3$ (b), H (c), Cl (d), F (e)

Scheme 1b  Fig. 2b

Scheme - 2  Fig. 3

Table 1.

| Solvent | Isomer | 5-OMe $\lambda_{max}$/nm ($\varepsilon_{max}$) | 5-Me $\lambda_{max}$/nm ($\varepsilon_{max}$) | 5-H $\lambda_{max}$/nm ($\varepsilon_{max}$) | 5-Cl $\lambda_{max}$/nm ($\varepsilon_{max}$) | 5-F $\lambda_{max}$/nm ($\varepsilon_{max}$) |
|---|---|---|---|---|---|---|
| Acetonitrile | E | 406 (18100) | 399 (16800) | 395 (13400) | 386 (15400) | 386 (14700) |
| | Z | 419 (20300) | \ | 419 (16000) | 405 (15300) | \ |
| | C | 531 (14900) | 523 (15900) | 514 (14100) | 510 (14400) | 513 (14100) |
| Methanol | E | 408 (18000) | 403 (17100) | 395 (13300) | 389 (15200) | 388 (14400) |
| | Z | 426 (22300) | \ | 423 (17000 0) | 409 (16400) | \ |
| | C | 530 (14500) | 522 (15400) | 512 (13700) | 509 (13800) | 512 (13600) |
| 1,2-Dichloro ethane | E | 411 (18900) | 407 (17700) | 403 (14100) | 394 (15700) | 393 (15100) |
| | Z | 429 (21300) | \ | 429 (16900) | 415 (16200) | \ |
| | C | 531 (15400) | 524 (16100) | 515 (14100) | 512 (12900) | 513 (14100) |
| Hexane | E | 405 (18700) | 400 (17200) | 398 (13500) | 387 (15800) | 385 (14600) |
| | Z | 428 (16400) | \ | 426 (18700) | 416 (18800) | \ |
| | C | 490 (14100) | 484 (14800) | 475 (13300) | 471 (13500) | 471 (13400) |

Fig. 4

Table 2.

| Substituent | φ E-C (λEX = 350 nm) | | | φ C-E (λEX = 495 nm) | | |
|---|---|---|---|---|---|---|
| | Acetonitrile | Dichloroethane | Hexane | Acetonitrile | Dichloroethane | Hexane |
| 5-H | 0.12 | 0.11 | 0.26 | 0.018 | 0.16 | 0.32 |
| 5-OMe | 0.093 | 0.063 | 0.16 | 0.00007 | 0.003 | 0.33 |
| 5-Me | 0.11 | 0.091 | 0.22 | 0.0011 | 0.015 | 0.29 |
| 5-Cl | 0.12 | 0.11 | 0.24 | 0.040 | 0.19 | 0.30 |
| 5-F | 0.13 | 0.11 | 0.24 | 0.022 | 0.15 | 0.33 |

Fig. 5

Table 3.

| Substituent | φE-Z (λEX = 350 nm) | | φ Z-E (λEX = 350 nm) | |
|---|---|---|---|---|
| | Acetonitrile | Hexane | Acetonitrile | Hexane |
| 5-H | 0.208 | 0.204 | 0.107 | 0.190 |
| 5-OMe | 0.348 | 0.639 | 0.275 | 0.889 |
| 5-Cl | 0.283 | 0.697 | 0.179 | 0.328 |

Fig. 6

Table 4

| Substituent | C/Co % | | | |
|---|---|---|---|---|
| | Acetonitrile | Dichloroethane | MMA | hexane |
| 5-OMe | \ | \ | 91 | \ |
| 5-Me | \ | \ | 91 | \ |
| 5-H | 90 | 93 | 92 | 87 |
| 5-Cl | 90 | \ | 91 | \ |
| 5-F | 95 | \ | 92 | \ |

Fig 7

Table 5.

| | Acetonitrile | | Dichloroethane | | Hexane | |
|---|---|---|---|---|---|---|
| Substituent | $\lambda$max (EM) | $\phi$FL | $\lambda$max (EM) | $\phi$FL | $\lambda$max (EM) | $\phi$FL |
| 5-OMe | 662 nm | 0.0008 | 650 nm | 0.0004 | 552 nm | \ |
| 5-Me | 635 nm | \ | \ | \ | 536 nm | \ |
| 5-H | 618 nm | 0.033 | 604 nm | 0.074 | 536 nm | 0.0003 |
| 5-Cl | 613 nm | 0.03 | 602 nm | 0.058 | 526 nm | \ |
| 5-F | 616 nm | \ | \ | \ | 526 nm | \ |

FLUORESCENT PHOTOCHROMIC FULGIDES, PARTICULARLY FOR OPTICAL MEMORIES

REFERENCE TO A RELATED PATENT APPLICATION

The present utility patent application is descended from U.S. provisional patent application Ser. No. 60/099,513 filed Sep. 8, 1998, for FLUORESCENT PHOTOCHROMIC FULGIDES recorded as FLUORESCENT PHTOCHROMIC FULGIDES [sic]. The contents of the related predecessor patent application are incorporated herein by reference.

This invention was made by support of the U.S. Government under Contracts Nos. F30602-97-C-0029 and F-30602-93-C-0232 acting through the United States Air Force, Rome Laboratory. The U.S. Government has certain rights in this invention.

BACKGROUND OF THE INVENTION

1. Field of the Invention

The present invention generally concerns fulgides, photochromism, and fluorescing photochromes.

The present invention particularly concerns stable fluorescing photochromic fulgides.

2. Description of the Prior Art

Photochromic fulgides, a class of organic compounds which are capable reversible light-induced coloration, were discovered by Stobbe and then further developed by several research groups. See Stobbe, *Berichte*, 40, 3372 (1907).

Photochromic fulgides exhibit several important physical properties, such as thermal stability of both colorless and colored forms, high photoreaction efficiency, high fatigue resistance to repeated coloration-bleaching cycles and light power. Photochromic fulgides are promising candidates for many technological applications including use in recording media, particularly in erasable optical memory devices. See D. A. Parthenopoulos and P. M. Rentzepis, *Journal of Molecular Structure*, 224,297 (1990).

For their utilization as 3D optical memory device materials—where the accessing of information is achieved by means of the fluorescence emitted by the written bits— the colored form of the photochromic material will desirably fluoresce when illuminated with light. See A. S. Dvornikov, S. Esener and P. M. Rentzepis, in J. Jahns and S. H. Lee (Eds.), *Optical 5. Computing Hardware*, Academic Press Inc., 1993, pp. 287–325. See also A. S. Dvornikov and P. M. Rentzepis, in R. A. Lessard and W. F. Frank (Eds.), *Polymer in optics: physics, chemistry and applications, Critical reviews of optical science and technology*, v. CR63, SPIE, 1996, pp. 239–261.

Recently, a series of heteroclic photochromic fulgides have been synthesized. See H. G. Heller and J. R. Langan, *J. Chem. Soc. Perkin Trans.* 2, 341 (1981); E A. Kaneko, A. Tomoda, M. Ishizuka, H. Suzuki, and Ryoka Matsushima, *Bull. Chem. Soc. Jpn.* 61, 3569 (1988); and H. G. Reller and S. Oliver, *Chem. Soc. Perkin Trans.* 1, 197 (1981).

These heteroclic photochromic fulgides are thermally stable, fatigue-resistant and undergo near-quantitative conversion to their colored forms upon exposure to UV light. However, these photochromic fulgides do not fluorescein either their colored or their colorless form. See A. S. Dvornikov and P. M. Rentzepis, in R. A. Lessard and W. F. Frank (Eds.), *Poiymer in optics: phtysics, chemistry and applications, Critical reviews of optical science and technology*, v. CR63, SPIE, 1996, pp. 239–261, op. cit.

To the best knowledge of the inventors no data has been published on any fluorescing fulgides. The synthesis and photochromic properties of some 2-indolyfulgides have been reported. See I. Y. Grishin, Y. M. Chunaev, N. M. Przhiyalgovskaya, and A. V. Metelit, *Khim. Geterotsikl. Soedin*, 3, 422 (1992); and I. Y. Grishin, N. M. Przhiyalgovskaya, Y. M. Chunaev. V. F Mandzhikov, L. N. Kurkovskaya, and N. N. Suvorov, *Khim. Geterotsikl. Soedin.*, 7, 907 (1989).

SUMMARY OF THE INVENTION

The present invention contemplates photochromic fulgides that are fluorescing or, more exactly, that can be induced to fluoresce by radiation of an appropriate frequency. The fluorescent photochromic fulgides of the present invention are particularly suitable for optical memories.

The fluorescent photochromic fulgides of the present invention exhibit all the important physical properties of photochromic fulgides; to wit: thermal stability of both colorless and colored forms, high photoreaction efficiency, high fatigue resistance to they repeated coloration-bleaching cycles and light power. Moreover, they are strongly fluorescent in one (only) stable form.

In one of its aspects the present invention is embodied in a photochromic chemical consisting essentially of colored fluorescent heterocyclic fulgides.

In another of its aspects the present invention is embodied in heterocyclic photochromic fulgides Consisting essentially of colored 2-indolyfulgides capable of excitation by at least ultraviolet light to fluoresce.

These heterocyclic photochromic fulgides are preferably synthesized by process of (1) condensation of 1,3-dimethyl-(5-substituted) indole -2-carboxaldehyde, with diethyl iospropylidenesuccinate as a key intermediate; followed by (2) hydrolysis; and (3) intramolecular acid anhydride formation.

Figure 2A:
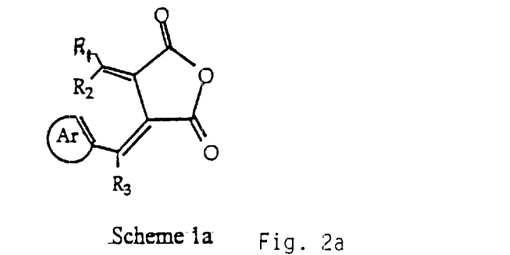

In yet another of its aspects the present invention is embodied in a family of molecules of the form shown in FIG. 2 where attached radical R is drawn from the group R=H; R=OCH$_3$; R=CH$_3$; R=Cl; and R=F.

These and other aspects and attributes of the present invention will become increasingly clear upon reference to the following drawings and accompanying specification.

BRIEF DESCRIPTION OF THE DRAWINGS

FIG. 2, consisting of FIG. 2a and FIG. 2b, is diagrammatic representation of the end products of a first scheme first variant, and first scheme second variant, for producing the fluorescent of the present invention.

DESCRIPTION OF THE PREFERRED EMBODIMENT

1. Introduction

A new class of thermally stable and fatigue resistant fluorescent photochromic 2-indolylfulgide derivatives have been synthesized. The absorption spectra, quantum yields of the photochemical reaction and fluorescence of these fulgides were measured and the solvent polarity dependent properties were also determined. Polar solvents were found to shift the absorption spectra of colored form to the longer wavelengths. The quantum yields of both coloration and bleaching process increased in nonpolar solvents, while the fluorescence quantum yields decreased. Electron donor substituents, at the 5-position of the indole ring shift the absorption spectra to longer wavelengths of both open and closed forms. The experimental data clearly show that substitution at the 5-position of the indole ring does not affect fatigue resistance. The solvent may affect the cycle fatigue.

The present specification teaches the synthesis and the photochromic behavior of these 2-indolyfulgides. As found by the inventors, the colored forms of those photochromic fulgides are capable to emit considerable fluorescence. Some five different species of 2-indolyfulgides were synthesized and unambiguously identified by means of NMR, MS and elemental analysis.

The photochromic fulgides of the present invention have high reversible photochemical reaction efficiency, long term thermal stability and, quite importantly, the colored form also fluoresces when irradiated with visible light.

2. The Synthesis of Photochromic Fluorescent 2-indolylfulqides

Fulgides, first investigated by Stobbe, are derivatives of dimethylene succinic anhydride. See H. Stobbe, Ber., 37 (1904) 2236.

For photochromic fulgides, at least one aryl group (usually heterocyclic aryl group) attached to the metheylene forming a 4n+2 system. See scheme 1a in FIG. 2a. When the open-ring form (known as colorless form) of these fulgides is irradiated with UV light, a conrotatory ring-closure reaction occurred according to the Woodward-Hoffman selection rules. See scheme 2 in FIG. 3.

This results in the formation of a cyclized structure (known as colored form or C form) whose absorption spectrum is red shifted to the visible region.

2.1 Preferred Synthesis Process

The synthesis of 2-indolylfulgides with a 5-substituted indole ring was achieved by Stobbe condensation of the corresponding 1,3-dimethyl-(5-substituted)indole-carboxaldehyde with diethyl iospropylidenesuccinate followed by hydrolysis and intramolecular acid anhydride formation. The subject compounds of the present invention have been synthesized according to the following process.

The preferred process of the present invention for making 1,3-dimethyl-2-indolylmethlene(isopropylidene)succinic anhydrides includes (1) mixing 1.3-Dimethyl-2-formylindole derivatives with diethyl iospropylidenesuccinate and a hydrocarbon solvent to form a first mixture; (2) stirring sodium hydride in a hydrocarbon solvent to form a second mixture; (3) adding the first mixture to the second mixture; (4) first stirring the combined mixtures at room temperature; (5) adding ice water; (6) extracting the combined do mixtures with a hydrocarbon solvent; (7) first-acidifying the aqueous layer with acid to give a crude half ester; (8) hydrolyzing the crude half ester by boiling with alcohol; (9) removing the ethyl alcohol under reduced pressure; (10) dissolving the potassinum salts in water; and (11) second-acidifying to give diacids; (12) treating the diacids so obtained with a solution of acetyl chloride; (13) stirring; (14) removing the solvent was removed, leaving a black oil; (15) eluting the black oil with chloroform-hexane as eluant; and (16) recrystallizing from the chloroform-hexane.

The (1) mixing of the 1,3-Dimethyl-2-formylindole derivatives with diethyl iospropylidenesuccinate and a hydrocarbon solvent is preferably in a 1:1:3 ratio.

The (1) mixing of the 1,3-Dimethyl-2-formylindole derivatives and diethyl iospropylidenesuccinate is preferably with the hydrocarbon solvent of toluene.

The (3) adding of the mixture to a stirred mixture of sodium hydride in toluene is preferably dropwise (i.e., drop by drop).

The (4) first-stirring of the combined mixtures at room temperature is preferably for at least 48 hours.

The (6) extracting of the mixture is preferably with the hydrocarbon solvent of benzene.

The (7) first-acidifying is preferably with hydrochloric acid, and more preferably with 5M hydrochloric acid.

The (8) hydrolyzing of the crude half ester is preferably by boiling with ethyl-alcohol, more preferably for at least 7 hours.

Alternatively, the hydrolyzing of the crude half ester may preferably be by boiling with 10% ethyl alcohol KOH.

The (9) removing of the ethyl alcohol under reduced pressure is by use of a rotary evaporator.

The (11) second-acidifying is preferably with hydrochloric acid, and is more preferably with 5M hydrochloric acids.

The (13) stirring is preferably in the dark, preferably for one and one-half hours.

Figure 1:
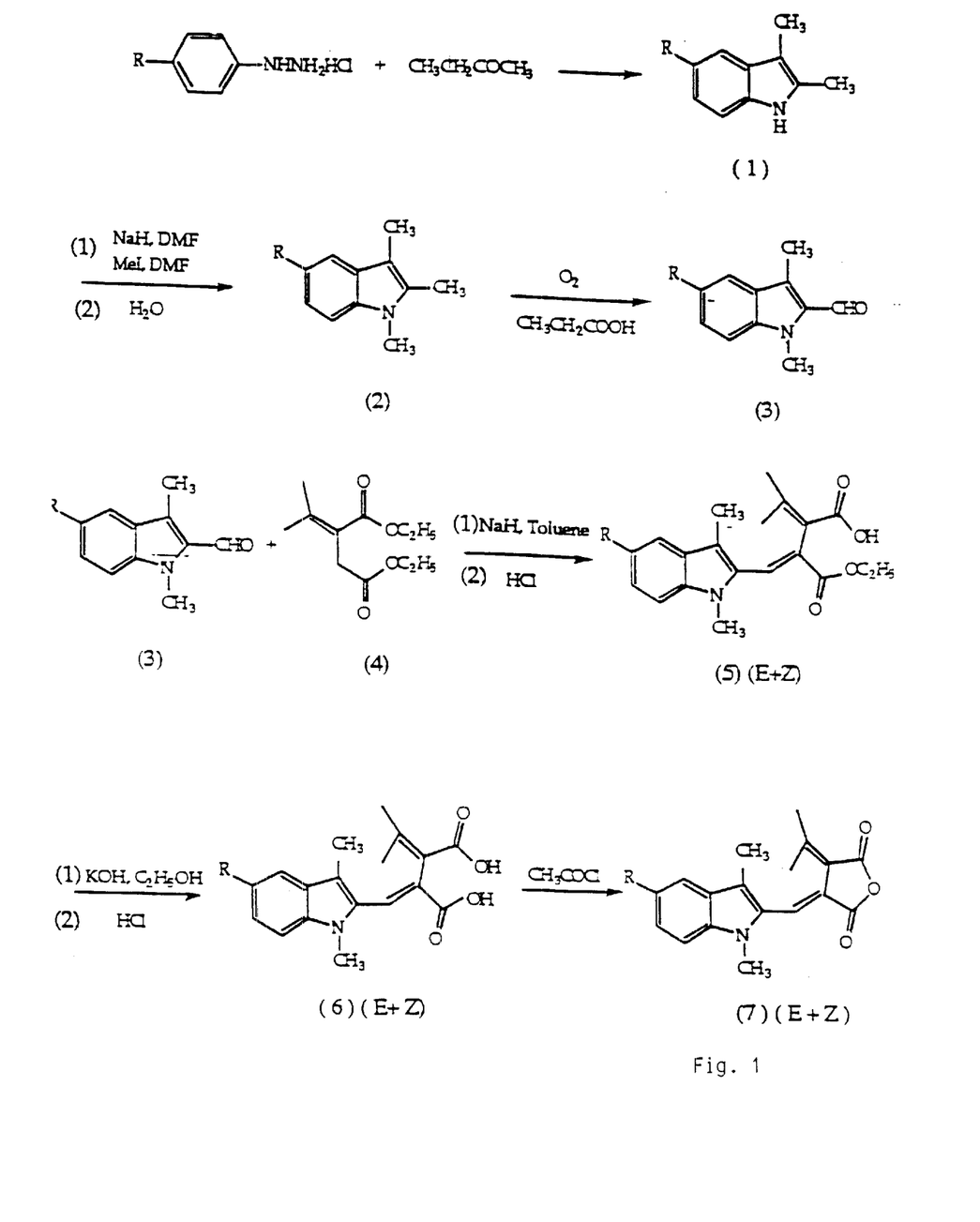
FIG. 1 is a diagram showing the stepwise process of synthesizing the fluorescent fulgides of the present invention.

This process is diagrammatically illustrated in FIG. 1. The synthesized fulgides of the present invention are all represented in the final step 7 of FIG. 1. At least five speies, called species "7a–7e", are both possible and of interest. In these species the attached atom or molecule R (see step 7 in FIG. 1) is as follows:

| Species | R = |
| --- | --- |
| 7a | H |
| 7b | $OCH_3$ |
| 7c | $CH_3$ |
| 7d | Cl |
| 7e | F |

Intermediates 2-methylindoles, 1,2,3-trimethylindoles and diethyl iospropylidenesuccinate were prepared by the methods described in D. W. Ockenden and K. Schofield, *J. Chem. Soc.*, 3175 (1957); T. Itahara, H. Ouya and K. Kozono, Bull. *Chem. Soc. Jpn.*, 55, 13861 (1982); and C. G. Overberger and C. W. Roberts, *J. Am. Chem. Soc.*, 71, 3618 (1949).

An effective method for the preparation of 2-formylindole by auto-oxidation of 2-methyl group of 1,2,3-trimethylindole in propionic acid has been reported. See T Itahara,: H. Ouya and K. Kozono, *Bull. Chem. Soc. Jpn.*, 55, 13861 (1982), op. cit.

The 5-substituted 1,3-dimethyl-2-formylindole derivatives (see Y. Yokoyama, T. Tanaka, T. Yamane and Y. Kurita, op. cit.), which are the key intermediates for the synthesis of the compounds (see H. G. Heller and J. R. Langan, op. cit.) were successfully prepared by using this method, but with increased reactant concentration and extended reaction time.

Figure 3:
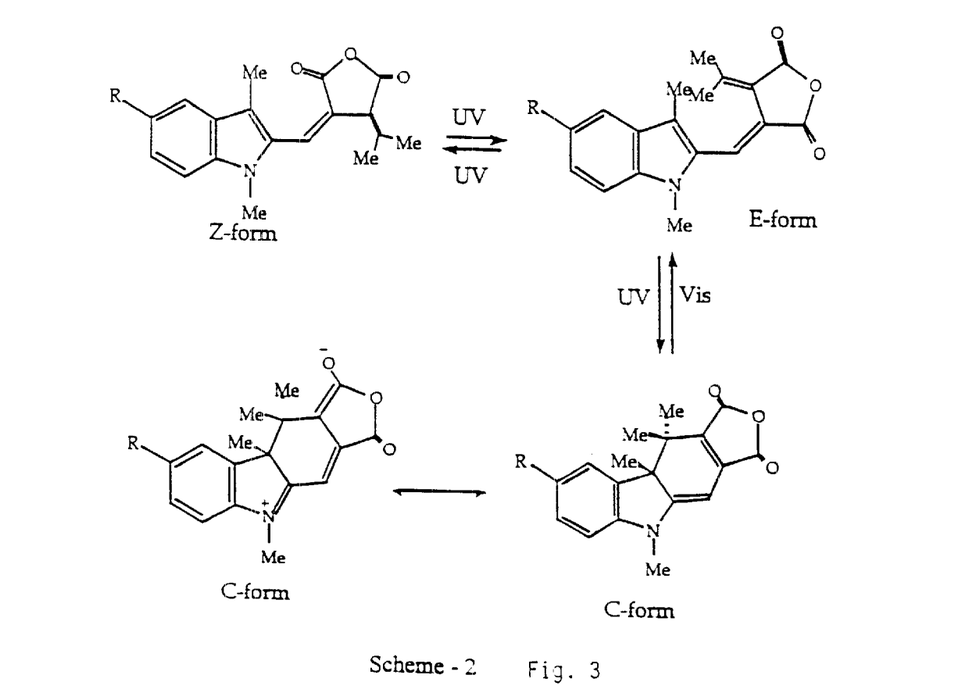
FIG. 3 is a diagrammatic view showing the reversible photoisomerization, ultimately generating the cyclic structure C shown at the bottom of FIG. 2, undergone by the synthesized fulgides of the present invention when illuminated with UV light.

2.2 Basic Photochromism and Spectroscopic Properties of the Fluorescent Fulcides of the Present Invention The synthesized fulgides-7a-7e were. found, when illuminated with UV light, to undergo reversible photoisomerization. A diagrammatic view of this reversible photoisomerization—scheme 2 of the present invention—is shown in FIG. 3. Photoisomerizable molecular structures "Z", "E" and C are each shown in FIG. 3. The structure of molecular species C which undergoes cyclically reversible photoisomization, also called photocylcyclization, is diagrammatically illustrated at the bottom of FIG. 3.

Initially light-yellow-colored solutions of species 7a–7e (produced by scheme 1 shown in FIG. 2) become red under excitation with 350–400 nm light.

In parallel with the photocyclization process the photoisomerization between E and Z forms also takes place, which can be observed by the shift of the long wavelength absorption band of the open form, if only either the E or Z forms are initially present. Because the absorption spectra of E and Z forms are slightly different, photoexcitation in the 350–400 nm region where both forms have strong absorption leads to the formation of the photoequilibrium mixture of these two forms which causes spectrum broadening.

The inventors were able to separate the E, Z and C forms by means of column chromatography and measure the individual spectra of each of these forms. The identities of the E, Z and, C forms were confirmed by their NMR spectra. The absorption spectra of the B, Z and C forms in acetonitrile has been measured. The absorption spectrum of the colored C form is red-shifted by –130 nm compared to the open form and, in addition, it exhibits a very low intensity absorption band in the region of 330–400 nm.

Because of the significant Stokest shift of the spectra, the inventors were able to convert the open form, almost quantitatively, into the cyclic colored form by light excitation at these wavelengths. The colored form can be reversibly bleached by excitation with $\lambda$>500 nm visible light. During the bleaching process only the formation of the E form was observed, which is the preferred configuration for the cyclization process.

It should be noted that when a solution of the Z form is excited with UV light, it also undergoes coloration due to the formation of the C form. Most probably this reaction proceeds via formation of the intermediate E form. The coloration/bleaching cycles were repeated 50 times without noticeable decomposition of the material.

All isomeric forms of these fulgides 7a–7e show excellent long term room temperature thermal stability. No changes were detected, by means of HNMR and UV-VIS absorption spectroscopy, when pure E, Z and C forms were dissolved in chloroform-d3, hexane and acetonitrile solvents and kept in the dark at room temperature for over a month. This data suggests strongly that no decomposition nor any other thermal reactions take place.

In contrast to other previously investigated fulgides (see, for example, A. S. Dvornikov, S. Esener and P. M. Rentzepis, op. cit.; and also A. S. Dvornikov and P. M. Rentzepis, op. cit.) the colored, form C, of the fulgides 7a–e, was found to emit red fluorescence when excited to its first allowed state. The fluorescence spectrum of the C form consists of a broad emission band with the maximum at about 610 nm.

To confirm that observed fluorescence indeed originated with colored forms of subject fulgides of the present invention, the inventors conduced measurements of fluorescence/intensity while solutions underwent sequences of bleaching-coloration cycles. The fluorescence intensity decreases with bleaching of the solution. When each solution was completely bleached with light $\lambda$>500 nm —i.e. no absorption band of C form at 515 nm was present—then no fluorescence was detected.

The fluorescence appeared again and rose up to the previous level when the solution was colored by UV light to the same optical density at maximum of absorption of the colored form. These data verify that fluorescence is induced by excitation of colored form of fulgide, rather than possible impurities or products of decomposition. The quantum yield of the fluorescence depends on substituent and solvent polarity, and varied between 0.03 and 0.13. The fluorescence spectrum is Stokes shifted by approximately 100 nm from the absorption. No fluorescence from the B or Z forms was detected.

2.3 A First Series of Heteryclic Photochromic Fulcides

A first series of species heteryclic photochromic fulgides in accordance with the present invention including, by way of example, 1,3-dimethylindole-2-carboxaldehyde, were produced, by way of example, dissolving 5g of 1,2,3-trimethylindole in 300 ml propionic acid and bubbling the solution with oxygen near the reflux temperature for 48 hours. The reaction mixture was evaporated to give a brown oily residue, which was purified by column chromatography and eluted with cyclohexane. 3.6 g of 1,3-dimethyl-2-formylindole was obtained. Other species are obtainable by the same process.

2.4 A Second Series of Heteryclic Photochromic Fulgides

A second series of species of heteryclic photochromic fulgides in accordance with the present invention including, by way of example 1,3-Dimethyl-2-indolylmethylene (isopropylidene)succinic anhydrides, were derived by the following general procedure.

A mixture of 1,3-dimethyl-2-formylindole derivatives (25 mmol) and diethyl isopropylidenesuccmate (25 mmol) mixed with toluene solvent was added dropwise to a stirred mixture of sodium hydride (75 mmol) in toluene. Subsequently, the reaction mixture was stirred at room temperature for 48 hours. Ice water was added. The mixture was extracted with benzene and the aqueous layer was acidified with 5M HCl. to give half ester. The crude half ester was hydrolyzed by boiling for 7 hours with 10% ethyl alcohol KOH. Then, the ethyl alcohol was removed under reduced pressure using a rotary evaporator. The potassium salts were dissolved in water and acidified with 5 M HCl: this produced diacids. The dried diacids obtained were treated with a solution of acetyl chloride and stirred in the dark at room temperature for one and half hours. Subsequently the solvent was removed, leaving a black oil which was on silica gel using chloroform-hexane as eluant. The title compound was obtained after recrystallization from chloroform-hexane.

3. The Effect of Solvent Polarity and Ring Substitution on the Photochromic Behavior and Pectroscopic Properties of Photochromic Fluorescent 2-indolylfulgides

3.1 UV-Vis Absorption Spectra of E, Z and C forms

Table 1 lists the absorption maxima of the E, Z and C isomers of fulgide a-e, in various solvents. The electronic absorption spectra of E-fulgides, at 385–408 nm, were found not be affected strongly by solvent. Substitutions of electron donor groups at the 5-position of the indole ring were found to shift the maximum absorption to longer wavelengths, while chloro and fluoro substituents at the same position shift the maximum absorption to shorter wavelengths, compared to 5-H fulgide. The maximum absorption of the Z-forms is in the region of 405 nm–429 nm, which is red shifted by about 20 nm compared to the corresponding E-forms. The X-ray data results show, in the open-ring fulgide form, the indole and anhydride components are not in a planar form, and consequently absorb in the blue region (390 nm), due to low conjugation between indole and anhydride parts. Upon irradiation with UV light, a near planar closed-ring structure was formed, resulting in a longer conjugated system which shifted the absorption to longer wavelengths. Longer wavelength shift in polar solvent and a high absorption extinction coefficient support the assignment of this E, Z and C-forms absorption to a $\pi$–$\pi^*$ transition See. D. A. Parthenopoulos and. P. M. Rentzepis, Journal of Molecular Structure, 224, (1990) 297.

Figure 4:
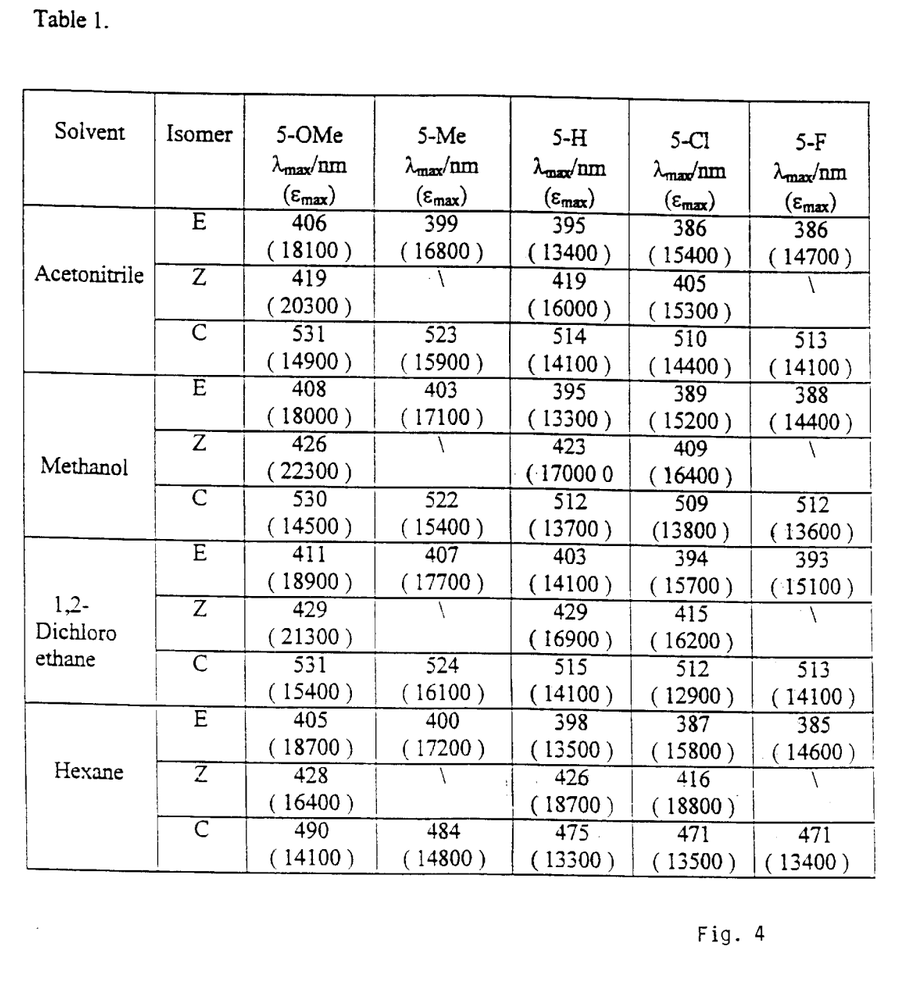
FIG. 4 is a Table 1 showing maximum absorption of 2-indolylfulgides in different solvents.

The E-form, Z-form and C-form absorption spectra of 1,3-Dimethyl-2-indolylmethlene-(isopropylidene) succinic anhydride in acetonitrile has been measured. The long wavelength absorption maxima and extinctions coefficients of these fulgides in different solvents are listed in, Table 1 shown in FIG. 4.

The maximum absorption of the C-form, was found to be located in the 470 to 530 nm-region, which is red shifted by about 120 nm compared to the corresponding open-ring forms. Polar solvents strongly affect the absorption maximum of the C form. This suggests that in the excited state, there is a large dipole molecule formed which is stabilized by polar solvents.

3.2 Photoreaction Ouantum Yield of 2-Indolylfulgide

Scheme 2 shown in FIG. 3 serves to synthesize fulgides of an open-ring form. When seven species of the synthesized open-ring form fulgides were illuminated with UV light, they underwent photoinduced electrocyclic reaction which generated the closed-ring structure C diagrammatically shown in Scheme 2 of FIG. 3. The initially light yellow colored solutions of the a-e open-ring form became red after excitation with 360 nm light. The absorption spectra changes, of (E)-1,3-Dimethyl-2-indolylmethlene-(isopropylidene) succinic anhydride in acetonitrile, induced by 360 nm light, was measured. In parallel with the ring-closing process, photoisomerization between E and Z forms also takes place, which is evident by the 20 nm shift in the isobestic a point. See FIG. 3.

The inventors have also observed the formation of the Z-form in the NMR spectra when pure E form was irradiated with UV light. Because of more than 100 nm Stockes shift of the absorption spectra of E and C and very low absorption of C form at 360 nm compared to that of E form, the inventors were able to convert the open form, almost quantitatively, to the cyclized colored form by 360 nm excitation of the E form in acetonitrile solvent. The colored form can be reversed back to the open-ring, bleached form, by excitation with $\lambda$>530 nm (with filter which cut below 530 nm). During the bleaching process only the formation of the E form was observed (see FIG. 3), which is the favorite configuration for the cyclization process.

It should be noted that, because the absorption spectra of the E and Z forms are only slightly different, photoexcitation in the 360 nm region, where both forms have strong absorption, leads to the formation of a photoequilibrium mixture between these two forms. This causes spectral broadening, therefore when a solution of the pure Z form, is excited with 360 nm light, it also generates the colored form but with a low quantum efficiency. Most probably this Z to colored form reaction proceeds via the formation of E form, as intermediate which in turn decays into the colored form.

Figure 5:
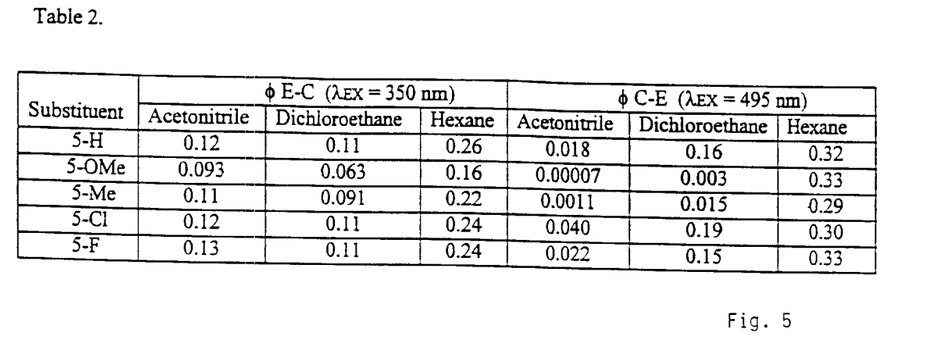
FIG. 5 is a Table 2 showing the quantum yield of photocoloration and photobleaching of 2-indolylfulgides in different solvents.

Table 2 shown in FIG. 5 lists the quantum yields of ring-closing (coloration) and ring-opening (bleaching) of 2-indolylfulgides in various solvents. These data show that, in polar solvents, such as acetonitrile, the quantum yield of E to C is about 0.1, while in nonpolar, hexane solvents, the quantum yield is increased by a factor of two compared to polar solvents. The quantum yield for the coloration processes is about the same as that of furylfulgide. See H. G. Heller, J. R. Langan, J.Chem.Soc.Perkin Trans.2, (1981) 341; and also Y. Yokoyama, H. Hayata, H. Ito, and Y. Kurita, Bull. Chem. Soc. Jpn. 63, (1990) 1607. The quantum yield for the coloration processes is also about the same as that of thienyl fulgide. See A. Tomoda, A. Kaneko, H. Tsuboi, and R. Matsushima, Bull.Chem.Soc.Jpn. 66, (1993) 330. The quantum yield for the coloration processes is, however, higher than that of 3-indolylfulgide. See Y. Yokoyama, T. Tanka, T. Yamane, and Y. Kurita, Chemistry Letters, (1991) 1125.

According to experimental results, the quantum yield of the bleaching process C to E, strongly depends on the polarity of the solvents. The fact that low quantum yield were observed in polar solvents may be explained by the existence of strong interaction between the charge separated excited state of the fulgide molecule and the polar solvents, which may have raised the reaction activation energy and therefore lower the transformation rate of the process. Electron donor substituent groups, such as methoxyl group, were found to stabilize strongly the colored form, and consequently reduce the bleaching quantum yield. This phenomenon was also observed with 3-indolylfulgides. See Y. Yokoyama, et al., op. cit. However, no photochromic reactions were deteiacted when 2-indolylfulgide crystals, were used instead of solution.

Figure 6:
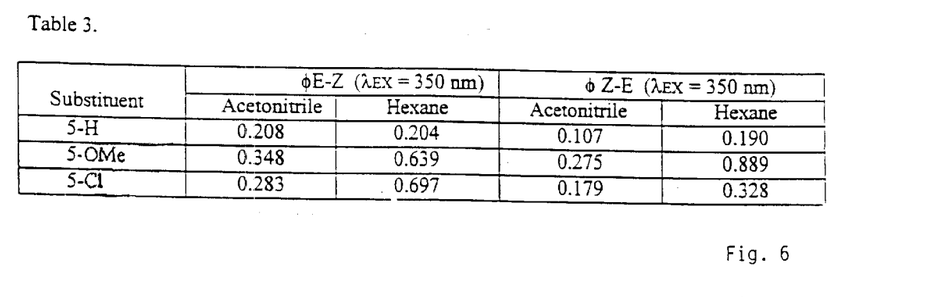
FIG. 6 is a Table 3 showing the quantum yield of 2-indolylfulgides E-Z-isomerization.

Table 3 shown in FIG. 6 shows the experimental quantum yields of the E-Z-isomerization for three-2-Indolylfulgides in polar acetonitrile and nonpolar hexane solvents. It is evident from the data that the quantum yield of the E-Z isomerization process, which competes with the coloration, has practically the same value as that of the coloration. The inventors believe that decreasing the rate of the E-Z isomerization will increase the coloration quantum yield.

3.3 Thermal Stability and Fatigue Resistance

Figure 7:
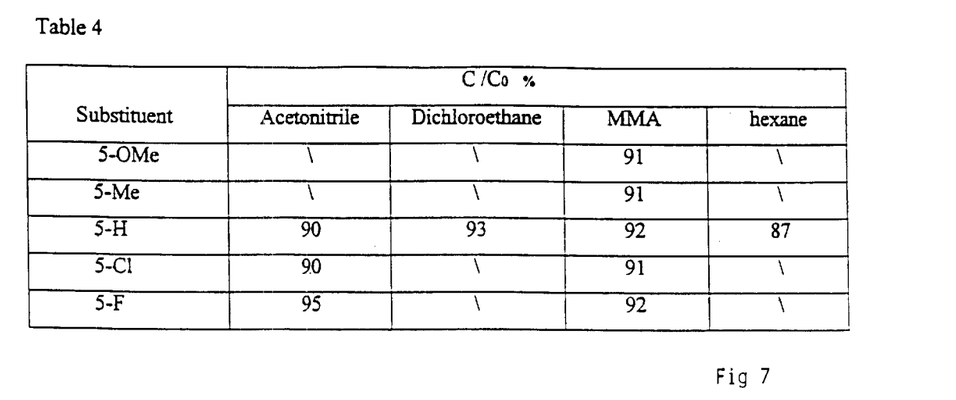
FIG. 7 is a table 4 showing the ratio of the nondecomposed fulgides to original forms after 100 complete coloration/bleaching cycles in various solvents.
Figure 9:
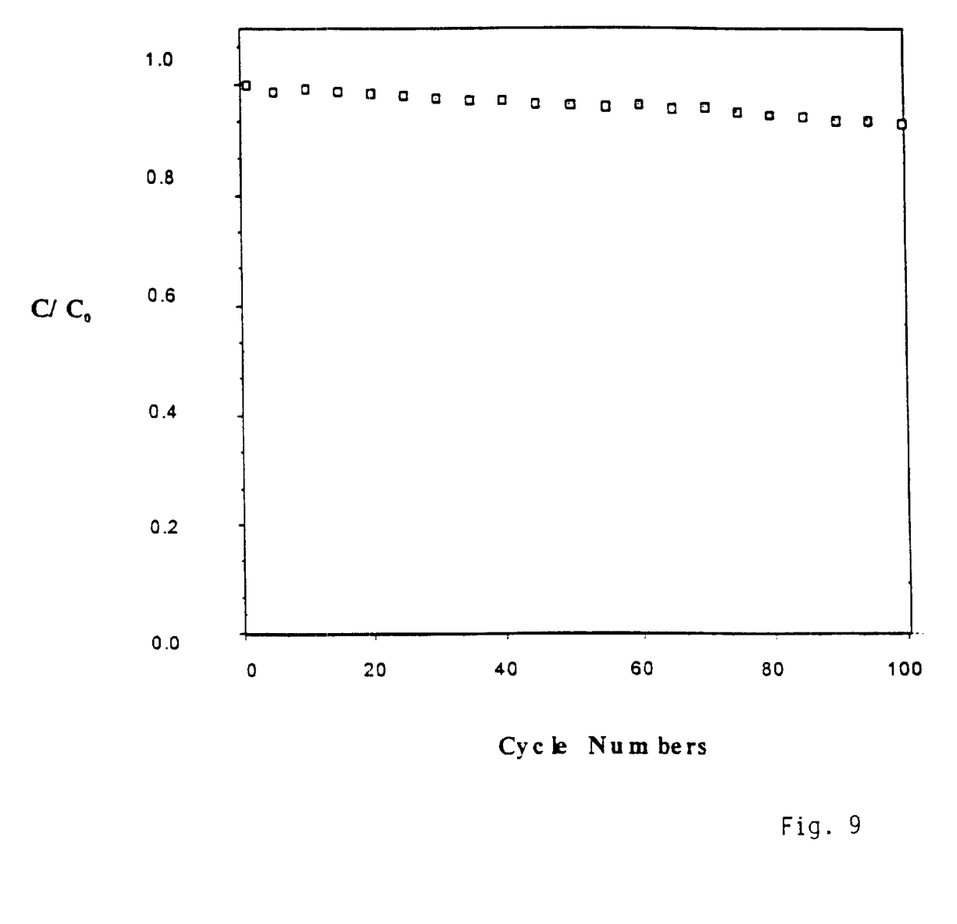
FIG. 9 is a graph of fatigue, defined as ratio of fulgide after 100 cycles to original, of 1,3-Dimethyl-2-indolylmethlene-(isopropylidene) succinic anhydride in, 1,2-dichloroethane, as a function of coloration/bleaching cycles.

Thermal stability of the media plays an important role in long-term information storage and electronic switching devices. Because of the possibility that these materials may be potential candidates as storage media, the inventors measured the thermal stability of E, Z and C-forms of these fulgides. Data shows that all the isomeric forms of fulgides, a-e, have excellent long term, room temperature, thermal stability. No changes, owing to temperature, were detected by means of -NMR and UV-Vis absorption spectroscopy, when pure E, Z and C forms were dissolved in chloroform-d3, hexane and acetonitrile solvents separately and kept in dark at room temperature for over one month. This data suggests, strongly, that no thermal decomposition or other thermal reactions occurred at room temperature during this long test period. We also investigated the fatigue resistance of our fulgides as a function of coloration/bleaching cycles. These data are shown in Table 4 of FIG. 7 and also in FIG. 9. Table 4 shows the ratio of the non-decomposed fulgides to original forms after 100 complete coloration/bleaching cycles in acetonitrile, MMA, 1,2-dichloroethane and hexane. The experimental data clearly show that substitution at the 5-position of the indole ring does not affect fatigue resistance. The solvent may affect the cycle fatigue, but not to a great extent.

3.4 Fluorescence Quantum Yield of 2-indolylfulqides

Figure 8:
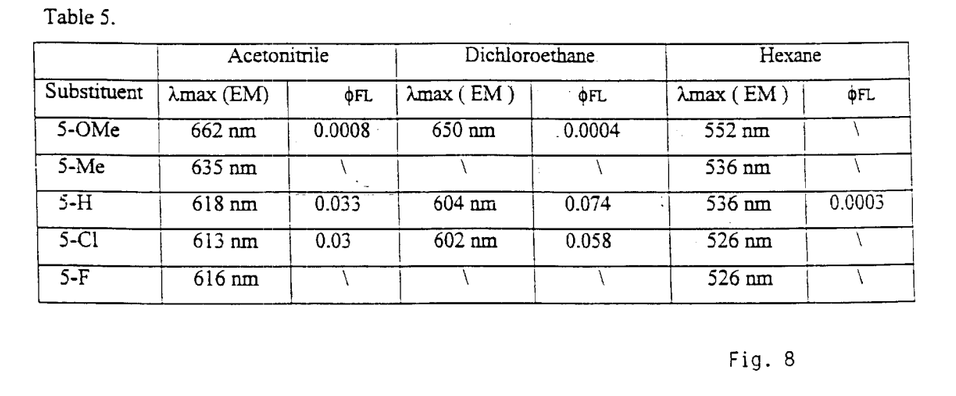
FIG. 8 is a Table 5 showing the fluorescence quantum yield of colored-2-indolylfulgides in various solvents

In contrast to the other previously investigated fulgides, the colored form C of fulgides synthesized by the inventors emit fluorescence. The fluorescence of the C form consists of a broad emission band with its maximum intensity in the range of 526 to 662 nm, which is in the sensitivity region of compact solid state detectors. The inventors found that the wavelength maximum depends on the polarity of the solvent and substituent. To confirm, that the observed fluorescence is-emitted by the colored forms of these fulgides rather than impurities or other species, the inventors measured the fluorescence intensity change as a function of bleaching/coloration cycles. The data show that the fluorescence intensity decreases proportionally with the bleaching of the fulgides. When the solution was completely bleached, with light, $\lambda > 530$ nm, i.e. the absorption band of the C form disappeared, no fluorescence was detected. The fluorescence appeared again and increased at the same rate as the rate of the growth of the C form. These data verify our statement that the fluorescence observed is due only to the colored form of fulgides, rather than any impurities or decomposition products. Table 5 of FIG. 8 shows the fluorescence quantum yield of the colored fulgides. The experimental data indicate that the quantum yield of the fluorescence depend on substituents and solvent polarity. When electron donor groups were substituted at the 5-position of the indole ring, decrease in the fluorescence quantum efficiency was observed. In contrast, relatively highs quantum yields were observed in polar solvents such as 1,2-dichloroethane as well as acetonitrile. The decrease of the quantum yields measured in nonpolar hexane may due to the increase in quantum yield of the photochemical reaction which compete with the fluorescence process.

The inventors have also investigated the possibility of the open E and Z fulgides for fluorescence, however they were not able to detect any emission from either form. The relatively low quantum yields of both fluorescence and photoreaction of the colored 5-Methoxy fulgide, are probably due to the highly efficient interconversion radiationless process.

4. Experimental Results

Figure 2B:
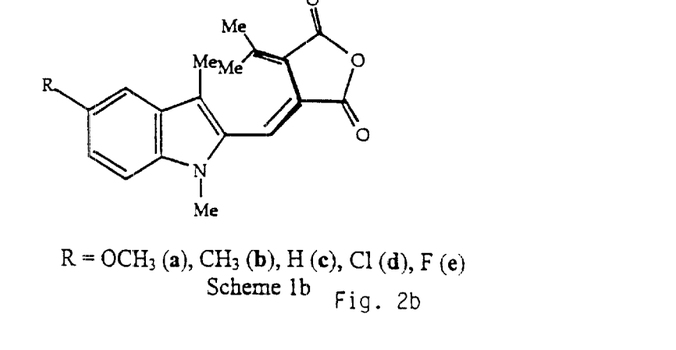

E and Z forms of fulgides obtained by scheme 1*b* shown in FIG. 2 were obtained directly by Stobbe condensation of the corresponding 1,3-dimethylindole-2-carboxaldehyde derivatives with diethyl iospropylidenesuccinate followed by column chromatography purification and then recrystallization. The colored forms (C-form) of these fulgides were prepared by irradiating, with 360 nm light, the E-form fulgides in an acetonitrile solution and the subsequent removal of the solvent under reduced pressure. The structure and purity of the compounds obtained were ascertained by NMR, MS and elemental analysis. All the solvents were HPLC grade or spectral grade and were used without further purification. All spectra and quantum yields were measured in 1 cm quartz cells at room temperature. The UV-VIS absorption and fluorescence spectra were recorded on a Shimadzu UV 160 spectrophotometer and a Shimadzu RF 5000U spectrofluorophotometer respectively.

Photoirradiation was carried out using a 150 W Xenon arc lamp (Oriel). Light of the appropriate wavelength was selected by either a monochromator or a cut off optical filter. The quantum yields of the photochromic reaction, ring-closing (coloration); and ring-opening (bleaching), were determined by comparison with the photochromic reaction yield of (E-2-[1-(2,5-Dimethyl-3-furyl) ethylidene]-3-isopropylidene succinic anhydride (Aberchrom 540) [13] in ethyl acetate. A mini magnetic stirring bar was used to mix the solution. The fluorescence quantum yield of the samples was determined by comparing the fluorescence intensity of our sample, with that of Rhodamin B in methanol solution which has a fluorescence quantum yield of 1.0.

5. Conclusion

A new class of thermally stable and fluorescing photochromic 2-indoly fulgide derivatives have been synthesized. The absorption and fluorescence spectra, the, quantum yields of fluorescence and the photochemical reactions of these fulgides were measured. The solvent polarity dependent properties were also studied. Polar solvents shift the absorption and fluorescence spectra to longer wavelengths. The quantum yields of coloration and bleaching process were found to be increased in nonpolar solvents, while the fluorescence quantum yields were decreased. The experiments of the inventors suggest that electron donor substituents at the 5-position of the indole ring, lead to longer wavelength absorption of both open and close forms. The stability of these fulgides as function of temperature and coloration/bleaching reversible cycles has also been determined.

Therefore the present invention will be recognized to be embodied in a photochromic chemical consisting essentially of colored fluorescent heterocyclic fulgides, and in a method of making such fluorescent heterocyclic fulgides.

The preferred fluorescent heterocyclic fulgides consist essentially of colored 2-indolyfulgides capable of excitation by at least ultraviolet light to fluoresce.

These heterocyclic photochromic fulgides are synthesized by process of (1) condensation of 1,3-dimethyl-(5-substituted)indole-2-carboxaldehyde with diethyl iospropylidenesuccinate as a key intermediate; followed by (2) hydrolysis; and (3) intramolecular acid anhydride formation.

This produces a family of molecules of the form shown in FIG. 2 where the attached radical R is drawn from the group R=H: R=OCH$_3$; R=CH$_3$; R=Cl; and R=F.

In accordance with the preceding explanation, variations and adaptations of the processes and materials in accordance with the present invention will suggest themselves to a practitioner of the hemical arts.

In accordance with these and other possible variations and adaptations of the present invention, the scope of the invention should be determined in accordance with the following claims, only, and not solely in accordance with that embodiment within which the invention has been taught.

What is claimed is:

1. A family of molecules suitable for use in an optical memory of the form where the attached radical R is drawn from the group consisting of H, OCH$_3$, CH$_3$, Cl, and F.

* * * * *